US00PP14600P29

(12) United States Plant Patent
Verwer

(10) Patent No.: US PP14,600 P2
(45) Date of Patent: Mar. 16, 2004

(54) DAHLIA PLANT NAMED 'KARMA YIN YANG'

(50) Latin Name: *Dahlia hybrida*
Varietal Denomination: Karma Yin Yang

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 10/437,941

(22) Filed: May 13, 2003

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—C. A. Whealy

(57) ABSTRACT

A distinct cultivar of Dahlia plant named 'Karma Yin Yang', characterized by its straight and strong flowering stems; freely basal branching growth habit; decorative-type inflorescence form; red purple and white bi-colored ray florets; excellent garden performance; and excellent inflorescence longevity.

2 Drawing Sheets

Botanical classification/cultivar designation: *Dahlia hybrida* cultivar Karna Yin Yang.

BACKGROUND OF THE INVENTION

The present Invention relates to a new and distinct cultivar of Dahlia plant, botanically known as *Dahlia hybrida* and hereinafter referred to by the name 'Karma Yin Yang'.

The new Dahlia is a product of a planned breeding program conducted by the Inventor in Lisse, The Netherlands. The objective of the breeding program is to create new cut flower Dahlia cultivars with straight strong flowering stems, decorative inflorescence form, attractive ray floret colors, and good inflorescence longevity.

The new Dahlia originated from a cross-pollination made by the Inventor in summer of 1997 of the *Dahlia hybrida* cultivar Wakamurasaki, not patented, as the female or seed parent with the *Dahlia hybrida* cultivar Karma Fuchsiana, not patented, as the male or pollen parent. The new Dahlia was discovered and selected by the Inventor as a single flowering plant within the progeny of the stated cross-pollination grown in a controlled environment in Lisse, The Netherlands, in the August, 1998. The selection of this plant was based on its strong straight stems and attractive ray floret coloration.

Asexual reproduction of the new Dahlia by cuttings was first conducted in a controlled environment in Lisse, The Netherlands in February, 1999. Asexual reproduction by cuttings has shown that the unique features of this new Dahlia are stable and reproduced true to type in successive generations.

SUMMARY OF THE INVENTION

The cultivar Karma Yin Yang has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Karma Yin Yang'. These characteristics in combination distinguish 'Karma Yin Yang' as a new and distinct Dahlia cultivar:

1. Straight and strong flowering stems.
2. Freely basal branching growth habit.
3. Decorative-type inflorescence form.
4. Red purple-colored ray florets with white apices.
5. Excellent garden performance.
6. Excellent inflorescence longevity.

Plants of the new Dahlia can be compared to plants of the female parent, the cultivar Wakamurasaki. However, in side-by-side comparisons conducted in Lisse, The Netherlands, plants of the new Dahlia differed from plants of the cultivar Wakamurasaki in the following characteristics:

1. Plants of the new Dahlia were taller than plants of the cultivar Wakamurasaki.
2. Plants of the new Dahlia had darker colored leaves than plants of the cultivar Wakamurasaki.
3. Plants of the new Dahlia had larger inflorescences than plants of the cultivar Wakamurasaki.
4. Ray florets of plants of the new Dahlia were red purple and white bi-colored whereas ray florets of plants of the cultivar Wakamurasaki were red and white bi-colored.

Plants of the new Dahlia can be compared to plants of the male parent, the cultivar Karma Fuchsiana. However, in side-by-side comparisons conducted in Lisse, The Netherlands, plants of the new Dahlia differed from plants of the cultivar Karma Fuchsiana in the following characteristics:

1. Plants of the new Dahlia were taller than plants of the cultivar Karma Fuchsiana.
2. Plants of the new Dahlia had darker colored leaves than plants of the cultivar Karma Fuchsiana.
3. Ray florets of plants of the new Dahlia were red purple and white bi-colored whereas ray florets of plants of the cultivar Karma Fuchsiana were red purple in color.

Plants of the new Dahlia are similar in ray floret coloration to plants of the cultivar Mystery Day, not patented. However, in side-by-side comparisons conducted in Lisse, The Netherlands, plants of the new Dahlia differed from plants of the cultivar Mystery Day in the following characteristics:

1. Plants of the new Dahlia were taller than plants of the cultivar Mystery Day.

2. Plants of the new Dahlia were more freely branching than plants of the cultivar Mystery Day.
3. Plants of the new Dahlia were more freely flowering than plants of the cultivar Mystery Day.
4. Plants of the new Dahlia had smaller inflorescences than plants of the cultivar Mystery Day.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of a typical flowering stem of 'Karma Yin Yang'.

The photograph on the second sheet is a close-up view of typical inflorescences of 'Karma Yin Yang'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three to four weeks after planting rooted cuttings. Plants were about four months old when the photographs and the description were taken.

Botanical classification: *Dahlia hybrida* cultivar Karma Yin Yang.

Parentage:

*Female, or seed, parent.*—*Dahlia hybrida* cultivar Wakamurasaki, not patented.

*Male, or pollen, parent.*—*Dahlia hybrida* cultivar Karma Fuchsiana, not patented.

Propagation:

*Type.*—By vegetative cuttings.

*Time to initiate roots.*—Summer: About 10 days at 18° C. Winter: About 13 days at 18° C.

*Time to produce a rooted young plant.*—Summer: About 23 days at 18° C. Winter: About 26 days at 18 to 20° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type inflorescence cut Dahlia. Straight and strong flowering stems; inverted triangle; vigorous.

*Plant height.*—About 110 cm.

*Plant diameter.*—About 35 cm.

*Flowering stem description.*—Quantity of flowering stems per plant: Pinched plants will produce about 24 flowering stems. Length: About 70 cm. Diameter: About 4 mm. Internode length: About 6 to 10 cm. Strength: Very strong. Aspect: Erect, straight. Texture: Glabrous, smooth. Color: 187A.

*Foliage description.*—Arrangement: Leaves opposite; leaves may be simple or compound with three or five leaflets. Shape: Ovate. Apex: Acuminate. Base: Attenuate. Margin: Entire or serrate. Length: Simple leaves: About 17 cm. Compound leaves with three leaflets: About 17 cm. Compound leaves with five leaflets: About 24 cm. Width: Single leaves: About 8 cm. Compound leaves with three leaflets: About 13 cm. Compound leaves with five leaflets: About 18 cm. Venation pattern: Pinnate. Texture: Smooth, glabrous; leathery. Color: Developing foliage, upper surface: 139A. Developing foliage, lower surface: 191A. Fully developed foliage, upper surface: 147A to darker than 147A. Fully developed foliage, lower surface: Darker than 148B. Venation, upper surface: Midvein, 187A; lateral veins, 146B. Venation, lower surface: Close to 146A. Petioles: Length: About 3 cm. Diameter: About 1 to 5 mm. Texture, upper and lower surfaces: Smooth, glabrous. Color, upper surface: 146B overlain with 187A. Color, lower surface: 146A.

Inflorescence description:

*Appearance.*—Decorative-type inflorescence form. Inflorescences borne on terminals, arising from leaf axils. Ray and disc florets develop acropetally on the receptacle. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 26 days in an outdoor environment. As cut flowers, inflorescences maintain good color and substance for about 7 to 8 days in an indoor environment.

*Quantity of inflorescences per flowering stem.*—One per lateral stem; about 24 inflorescences per plant develop during the growing season.

*Inflorescence size.*—Shape, in profile: Roughly hemispherical. Diameter: About 11 cm. Depth (height): About 4 cm. Diameter of disc: About 2 cm; inconspicuous. Receptacle diameter: About 1.6 cm. Receptacle height: About 6 mm.

*Inflorescence buds (just before opening).*—Length: About 1.2 cm. Diameter: About 2.1 cm. Shape: Oblate. Color: 153A.

*Ray florets.*—Length, fully developed: About 5 cm. Width, fully developed: About 2 cm. Shape: Elongated oblong. Apex: Mucronate. Base: Attenuate. Margin: Entire. Texture: Smooth, glabrous; satiny. Number of ray florets per inflorescence: About 120 arranged in about 20 rows. Venation pattern: Parallel. Color: When opening, upper surface: 59A; towards the apex, 60A; at apex, more white than 155B; apical margin, 64B. When opening, lower surface: 71A; 157B along the veins; towards the apex, 155A. Fully opened, upper surface: Basal half, 60A; towards the apex, 64A; at apex, 155C. Fully opened, lower surface: 71A; 157C along the veins; towards apex, 157D.

*Disc florets.*—Number of disc florets per inflorescence: About 27. Shape: Tubular, elongated. Apex: Five-pointed. Base: Attenuate. Length: About 7 mm. Diameter, apex: About 0.8 mm. Diameter, base: About 0.5 mm. Color: Immature: 7A. Mature: Apex: 21B. Mid-section: 23A. Base: Close to 1A.

*Phyllaries.*—Quantity: One whorl with about 9 phyllaries. Shape: Ovate. Apex: Acute. Base: Attenuate. Margin: Entire. Length: About 1.5 cm. Width: About 5 mm. Texture, upper and lower surfaces: Smooth, glabrous. Color, upper surface: 147A overlain with 187A. Color, lower surface: 148A overlain with 187A.

*Peduncles.*—Length, terminal peduncle: About 80 cm. Length, fourth peduncle: About 25 cm. Length, seventh peduncle: About 22 cm. Diameter: About 3 mm. Strength: Strong. Texture: Smooth, glabrous. Color: 187A.

*Reproductive organs.*—Androecium: Present on disc florets only. Stamen quantity: About five per floret. Anther length: About 7 mm. Anther color: 16A. Pollen amount: Scarce. Pollen color: 21B. Gynoecium: Present on ray and disc florets. Pistil quantity: One per floret. Pistil length: About 3 mm. Stigma color: Close to 12B. Style length: About 3 mm. Style color: 150B. Ovary color: 8A.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Karma Yin Yang', as illustrated and described.

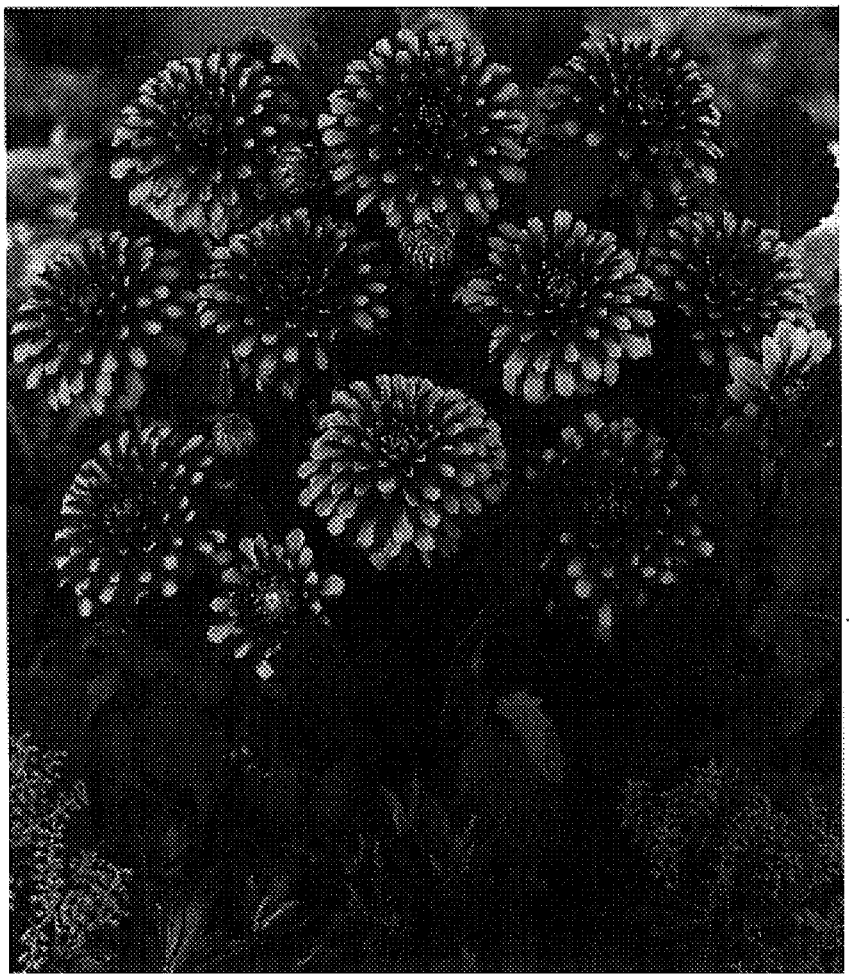

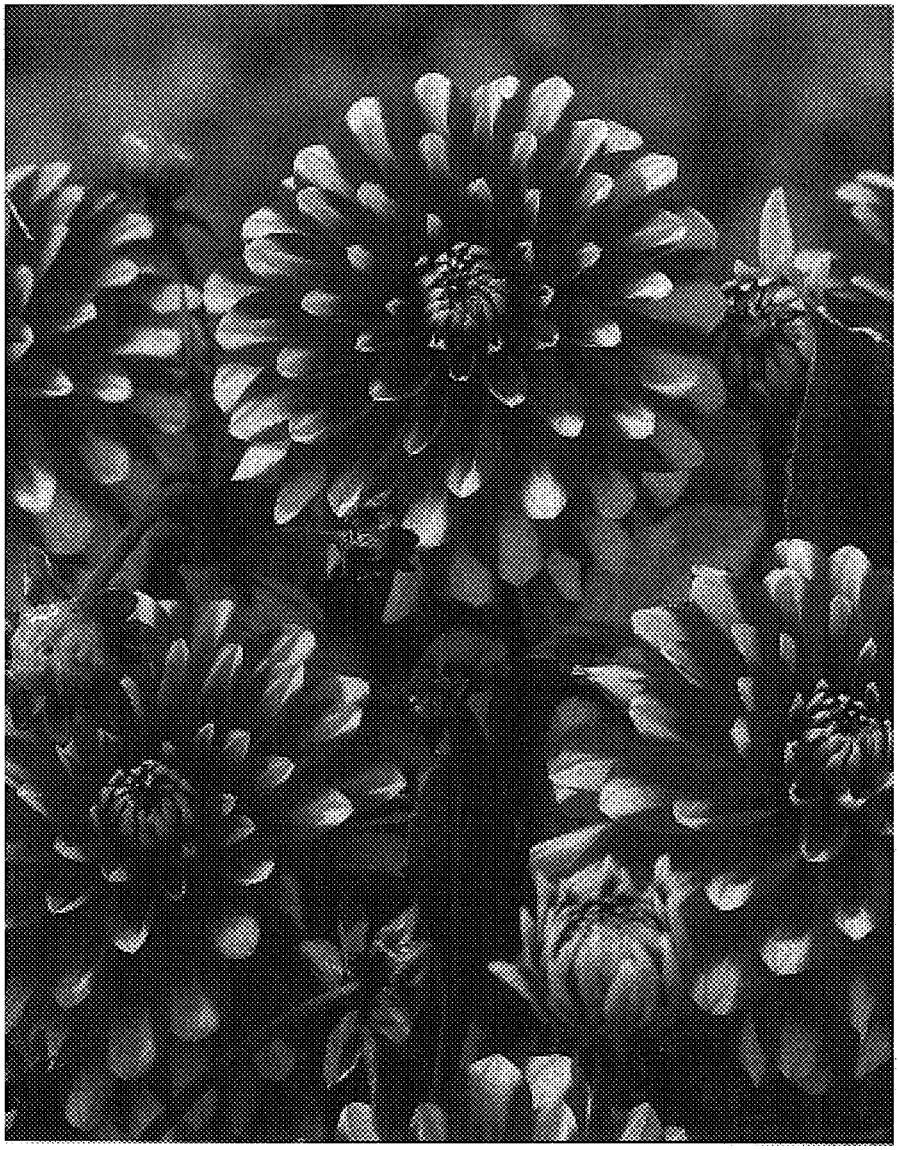

* * * * *